(12) United States Patent
Chen et al.

(10) Patent No.: US 10,663,396 B2
(45) Date of Patent: May 26, 2020

(54) REFRIGERANT ANALYZER AND A METHOD OF USING THE SAME

(71) Applicant: Carrier Corporation, Jupiter, FL (US)

(72) Inventors: Lei Chen, South Windsor, CT (US); Zhiwei Yang, South Windsor, CT (US); Farley William Postgate, Syracuse, NY (US); Warren Clough, Cicero, NY (US); Ivan Rydkin, Rochester, NY (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 178 days.

(21) Appl. No.: 15/748,112

(22) PCT Filed: Jul. 28, 2016

(86) PCT No.: PCT/US2016/044578
§ 371 (c)(1),
(2) Date: Jan. 26, 2018

(87) PCT Pub. No.: WO2017/019909
PCT Pub. Date: Feb. 2, 2017

(65) Prior Publication Data
US 2018/0356337 A1   Dec. 13, 2018

Related U.S. Application Data

(60) Provisional application No. 62/197,778, filed on Jul. 28, 2015.

(51) Int. Cl.
*G01N 21/3504* (2014.01)
*G01N 27/27* (2006.01)
(Continued)

(52) U.S. Cl.
CPC ......... *G01N 21/3504* (2013.01); *G01N 27/27* (2013.01); *G01N 33/0032* (2013.01);
(Continued)

(58) Field of Classification Search
CPC .... G01N 21/3504; G01N 21/61; G01N 21/94; G01N 27/27; G01N 33/0009; G01N 33/0027; G01N 33/0031; G01N 33/0032
(Continued)

(56) References Cited

U.S. PATENT DOCUMENTS

| | | | |
|---|---|---|---|
| 1,864,544 | A | 6/1932 | Lamb |
| 4,670,405 | A | 6/1987 | Stetter et al. |

(Continued)

FOREIGN PATENT DOCUMENTS

| | | |
|---|---|---|
| CN | 101836060 A | 9/2010 |
| CN | 203178248 U | 9/2013 |

(Continued)

OTHER PUBLICATIONS

PCT/US2016/044578, European Patent Office, International Search Report, dated Nov. 14, 2016.

(Continued)

*Primary Examiner* — Benjamin R Schmitt
(74) *Attorney, Agent, or Firm* — Cantor Colburn LLP (57) ABSTRACT

A method and an analyzer for detecting impurities in refrigerant (e.g. methyl chloride (R40) or Chlorodifluoromethane (R22)), wherein the refrigerant analyzer (12) includes a first sensing device (16), preferably a non-dispersive infrared sensor (NDIR), in flow communication with a second sensing device (18), preferably an electrochemical sensor. The first sensing device is configured to determine a first characteristic of a refrigerant (e.g. absorbance in the IR range), and the second sensing device is configured to detect a second characteristic of the refrigerant (e.g. concentration in (Continued)

ppmv). Preferably, the refrigerant analyzer is a part of a system for detecting impurities (10) and further preferably it comprises flow regulators (20), a scrubber (24) and a processor (22). The scrubber is preferably in flow communication with the first sensing device and it preferably comprises a packing material comprising alumina (Al2O3, aluminum oxide).

16 Claims, 6 Drawing Sheets

(51) Int. Cl.
*G01N 33/00* (2006.01)
*G01N 27/407* (2006.01)
*G01N 21/61* (2006.01)
*G01N 21/94* (2006.01)

(52) U.S. Cl.
CPC ............ *G01N 21/61* (2013.01); *G01N 21/94* (2013.01); *G01N 27/4072* (2013.01); *G01N 27/4074* (2013.01)

(58) Field of Classification Search
USPC .................................. 73/23.2, 31.03, 31.05
See application file for complete search history.

(56) References Cited

U.S. PATENT DOCUMENTS

| | | |
|---|---|---|
| 5,025,653 A | 6/1991 | Schuldt |
| 5,184,015 A | 2/1993 | Allman et al. |
| 5,363,661 A | 11/1994 | Condit et al. |
| 5,511,409 A * | 4/1996 | Knaebel ............ B01D 53/0454 73/28.04 |
| 5,731,510 A | 3/1998 | Jones et al. |
| 5,918,257 A | 6/1999 | Mifsud et al. |
| 6,085,576 A | 7/2000 | Sunshine et al. |
| 6,670,613 B2 | 12/2003 | Prozzo et al. |
| 7,756,683 B2 | 7/2010 | Kilgus |
| 8,586,383 B2 | 11/2013 | Walte et al. |
| 8,852,950 B2 | 10/2014 | Hoyer et al. |
| 2004/0022670 A1 | 2/2004 | Megerle et al. |
| 2004/0024278 A1 | 2/2004 | Megerle |
| 2004/0149912 A1 * | 8/2004 | Nomura ............. G01N 21/3504 250/339.13 |
| 2005/0287043 A1 | 12/2005 | Stromereder et al. |
| 2009/0189077 A1 | 7/2009 | Bivens et al. |
| 2012/0057161 A1 | 3/2012 | Tkachuk et al. |
| 2012/0185179 A1 | 7/2012 | Zhou et al. |
| 2013/0153060 A1 | 6/2013 | Barrett |

FOREIGN PATENT DOCUMENTS

| | | |
|---|---|---|
| EP | 1398618 A2 | 3/2004 |
| GB | 2239852 A | 7/1991 |
| WO | 2013066316 A1 | 6/2013 |
| WO | 2016029005 A1 | 2/2016 |
| WO | 2016105951 A1 | 2/2016 |

OTHER PUBLICATIONS

PCT/US2016/044578, European Patent Office, Written Opinion of the International Searching Authority, dated Nov. 14, 2016.

Lawton, Richard, Composition Analysis of Contaminated and Counterfeit Refrigerants Using the Agilent 490 Micro GC, Agilent Technologies, Inc., Jul. 8, 2015.

Singapore Search Report and Written Opinion for application 11201800702P, dated Apr. 5, 2019, 9 pages.

* cited by examiner

| SCENARIO | FIRST SENSOR RESPONSE | SECOND SENSOR RESPONSE | OUTCOME |
|---|---|---|---|
| 1. | YES | YES | R40 |
| 2. | YES | UNDETECTABLE | R22 OR R40 < 1000 ppmv |

*FIG. 6*

| SCENARIO | FIRST SENSOR RESPONSE | SECOND SENSOR RESPONSE | OUTCOME |
|---|---|---|---|
| 1. | YES | YES | R40 |
| 2. | YES | UNDETECTABLE | R22 OR R40 < 1000 ppmv, MOVE TO STEP 3 |
| 3. | | | |
| 3.1 | ABATED ABSORBANCE AFTER SCRUBBING | UNDETECTABLEE | R40, LESS THAN 1000 ppmv |
| 3.2 | UNCHANGED RESPONSE AFTER SCRUBBING | UNDETECTABLE | R22 |

*FIG. 7*

REFRIGERANT ANALYZER AND A METHOD OF USING THE SAME

CROSS-REFERENCE TO RELATED APPLICATIONS

The present application is an nonprovisional patent application, which claims priority to International Patent Application Serial No. PCT/US2016/044578, filed Jul. 28, 2016 and U.S. Provisional Patent Application Ser. No. 62/197,778, filed Jul. 28, 2015, and having the title "REFRIGERANT ANALYZER AND A METHOD OF USING THE SAME," which are herein incorporated in their entirety.

TECHNICAL FIELD OF THE DISCLOSED EMBODIMENTS

The presently disclosed embodiments generally relate to devices used for identification and analysis of impurities in refrigerant gas and more particularly, to a refrigerant analyzer and a method of using the same.

BACKGROUND OF THE DISCLOSED EMBODIMENTS

Counterfeit refrigerants, such as methyl chloride (R40) also known as chloromethane, have been found in refrigeration systems. R40 is toxic, flammable and reactive with aluminum. A reaction product of R40 with aluminum can include as trimethyl aluminum, which can burn spontaneously in the presence of air. There is therefore a need for a device to aid in the detection of counterfeit refrigerants, namely R40.

SUMMARY OF THE DISCLOSED EMBODIMENTS

In one aspect, a method of detecting impurities in a refrigerant utilizing a refrigerant analyzer, wherein the refrigerant analyzer includes a first sensing device in flow communication with a second sensing device is provided. The method comprises passing a refrigerant through the first sensing device to detect a first characteristic of the refrigerant; and passing the refrigerant through the second sensing device to detect a second characteristic of the refrigerant.

In one aspect, a refrigerant analyzer is provided. The refrigerant analyzer includes a first sensing device, wherein the first sensing device is configured at least to determine a first characteristic of a refrigerant, and a second sensing device in flow communication with the first sensing device, the second sensing device configured at least to determine a second characteristic of the refrigerant.

DETAILED DESCRIPTION OF THE DISCLOSED EMBODIMENTS

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1:
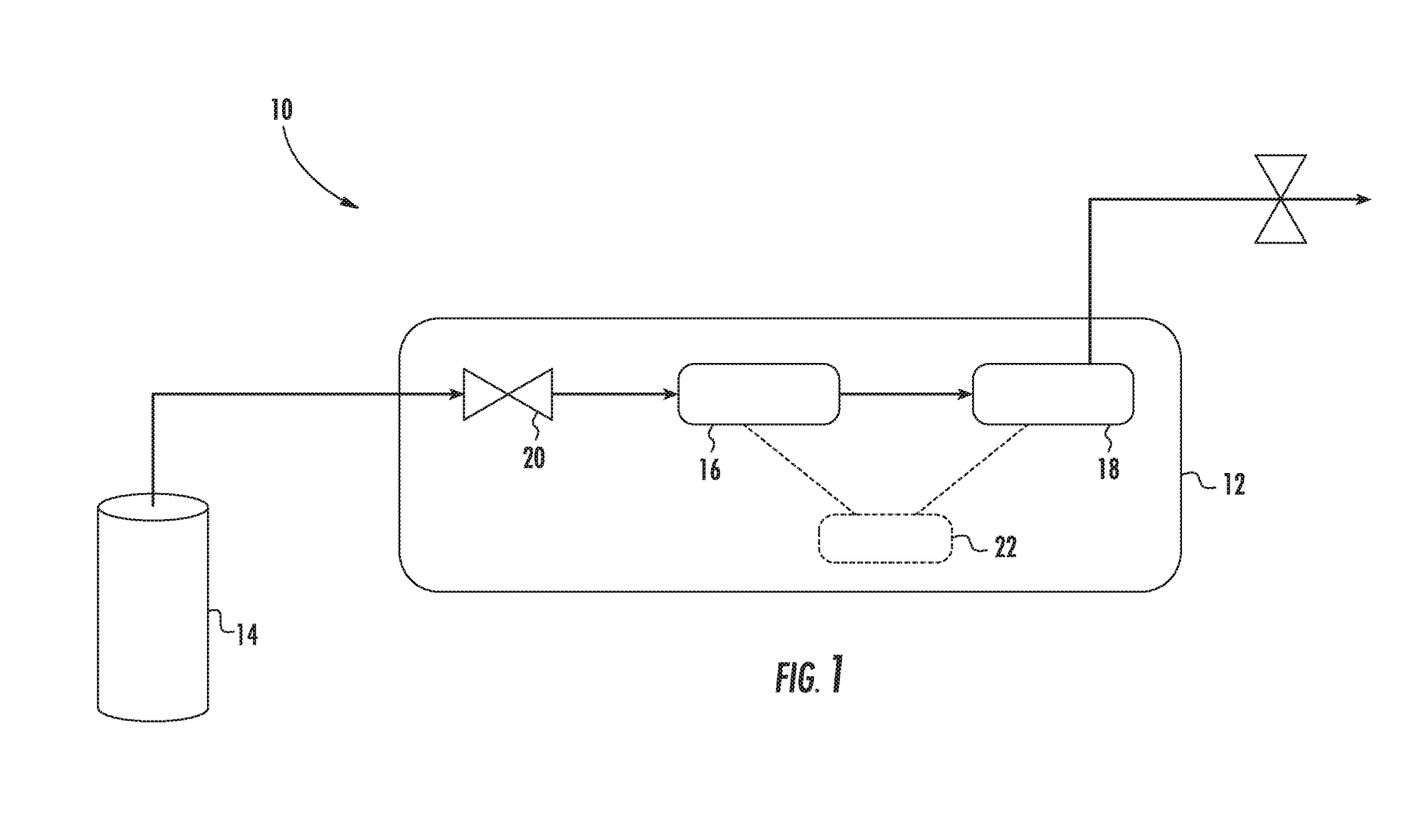
FIG. 1 illustrates a schematic drawing of gas detector including multiple sensors.

FIG. 1 illustrates a system for detecting impurities within a refrigerant, namely methyl chloride, the system generally indicated at 10. The system 10 includes a refrigerant analyzer 12 in flow communication with a refrigerant vessel 14.

The refrigerant analyzer 12 includes a first sensing device 16 configured at least to determine a first characteristic of a refrigerant. In an embodiment, the first characteristic includes a wavelength of electromagnetic energy absorbed by the refrigerant. In one embodiment, the wavelength is less than or equal to approximately 15,500 nanometers. For example, the first sensing device 16 is configured to at least detect low concentrations of impurities within the refrigerant. In an embodiment, the first sensing device 16 includes a non-dispersive infrared sensor.

The refrigerant analyzer 12 further includes a second sensing device 18 in flow communication with the first sensing device 16. The second sensing device 18 is configured at least to determine a second characteristic of the refrigerant. In an embodiment, the second characteristic includes a measured concentration level based at least in part on a sensed electronic output. In one embodiment, the measured concentration level is greater than or equal to approximately 1000 parts per million, volume based (ppmv). In an embodiment, the second sensing device 18 includes an electrochemical sensor. Alternatively, the refrigerant to be examined can be fed the first sensing device 16 and the second sensing device 18 in parallel as opposed to sequentially as illustrated in FIG. 1.

In the embodiment of FIG. 1, the refrigerant analyzer 12 includes a first flow regulator 20 in flow communication with the first sensing device 16. The first flow regulator 20 is configured at least to regulate the flow of refrigerant from the refrigerant vessel 14 through the refrigerant analyzer 12. The refrigerant analyzer 12 may further include a processor 22 in electrical communication with the first sensing device 16 and the second sensing device 18. The processor 22 is configured to receive data from the first sensing device 16 and the second sensing device 18 and/or generate an alert signal if a contaminant is detected.

Figure 2:
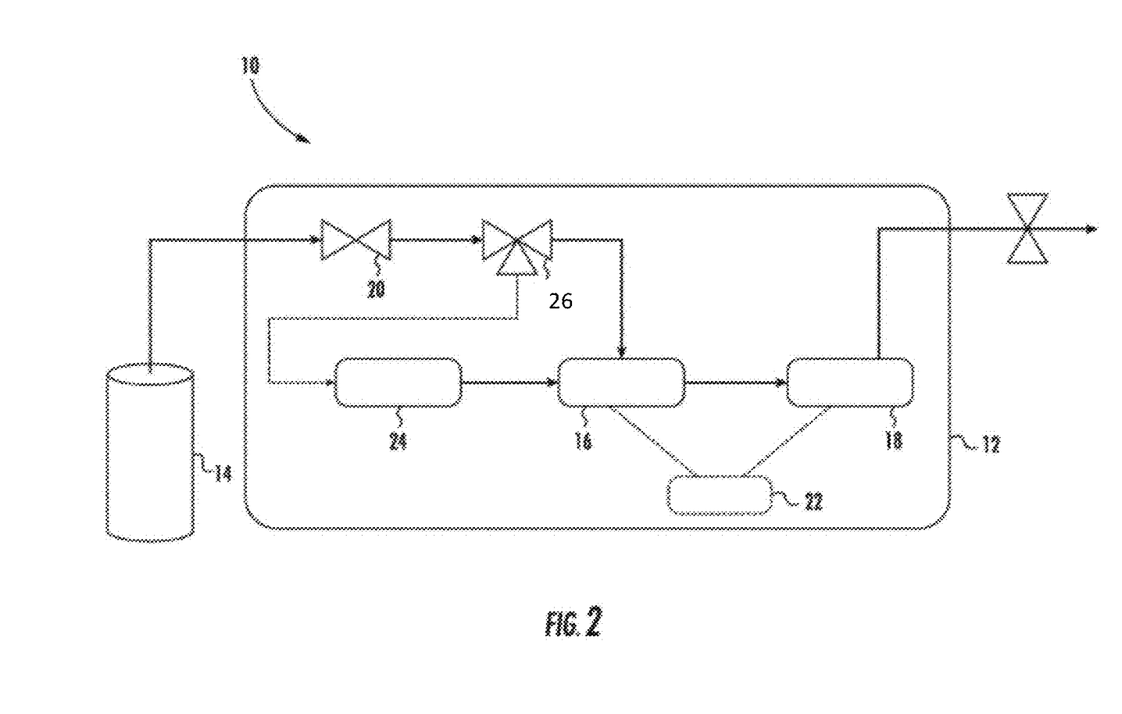
FIG. 2 illustrates a schematic drawing of gas detector including multiple sensors and a scrubber.

As shown in FIG. 2, the refrigerant analyzer 12 may include a scrubber 24 in flow communication with the first sensing device 16 and the second sensing device 18. In an embodiment, the scrubber 24 includes a porous alumina scrubber. For example, such a scrubber 24 can include a cartridge packed with alumina pellets for adsorption of R40 onto the surface of the pellets. Such a cartridge can be reusable, refillable, replaceable or a combination including at least one of the foregoing for ease of use by field technicians. The scrubber 24 is configured to selectively remove some impurities within the refrigerant to create distinguishable responses between the first sensing device 16 and the second sensing device 18 for accurate identification and quantification of impurities.

In FIG. 2, the refrigerant analyzer 12 can further includes a second flow regulator 26 in flow communication with the first sensing device 16, the first flow regulator 20 and the dry scrubber 24. The first flow regulator 20 can be configured at least to regulate the flow of refrigerant through the refrigerant analyzer 12. The second flow regulator 26 (e.g., an automatic 3-way valve to name just one non-limiting example) can direct refrigerant to flow either through the scrubber 24 or by-pass the scrubber 24 to enter the first sensing device 16.

Figure 3:
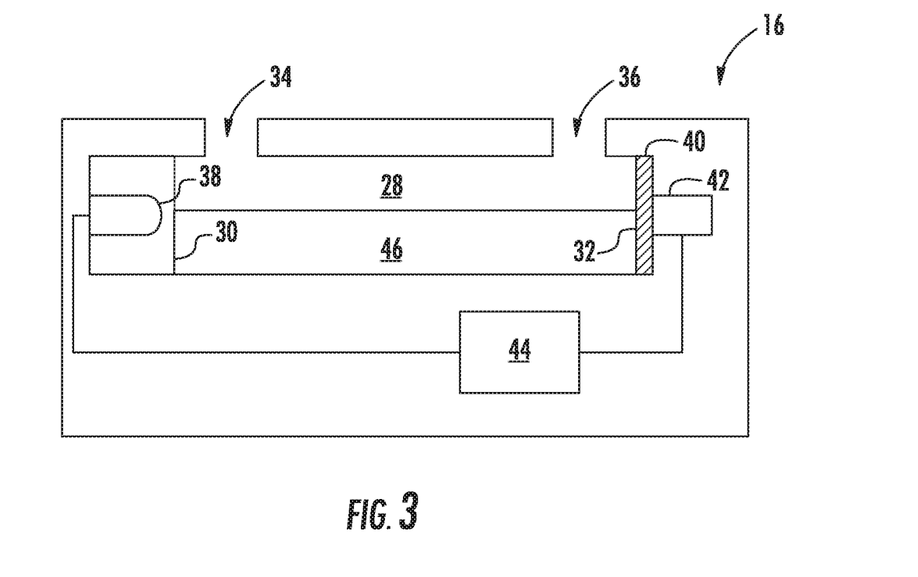
FIG. 3 illustrates a schematic diagram of a constituent optical sensor.

FIG. 3 illustrates the first sensing device 16 which can include a sample chamber 28 including a proximal end 30, a distal end 32, an inlet port 34, and an outlet port 36. The sample chamber 28 can be configured to allow refrigerant to flow therethrough without changing the composition of the refrigerant. For example, a refrigerant may enter the sample chamber 28 through the inlet port 34 and exit through the outlet port 36.

The first sensing device 16 further includes an infrared lamp 38. The infrared lamp 38 may be disposed anywhere within or adjacent to the sample chamber 28. For example, the infrared lamp 38 can be located adjacent to the proximal end 30 of the sample chamber 28. The infrared lamp 38 may be configured to direct infrared light through the sample chamber 28. The first sensing device 16 may further include an optical filter 40. The optical filter 40 can be disposed within or adjacent to the sample chamber 28. For example, the optical filter 40 can be located adjacent to the distal end 32 of the sample chamber 28. The optical filter 40 can be configured to eliminate all light except the wavelength region that selected gas molecules can absorb.

For example, the optical filter 40 may be configured to transmit a wavelength less than or equal to approximately 15,500 nanometers. To detect the presence of a refrigerant of interest, the optical filter 40 may transmit a wavelength greater than or equal to approximately 13,000 nanometers and less than or equal to approximately 15,000 nanometers.

The first sensing device 16 further includes a non-dispersive infrared sensor 42. The non-dispersive infrared sensor 42 can be disposed adjacent to the optical filter 40 and facing the infrared lamp 38. For example, the optical filter 40 can be positioned between the infrared lamp 38 and the non-dispersive infrared sensor 42. The non-dispersive infrared sensor 42 can measure the energy of the light from the infrared lamp 38 after it has passed through the refrigerant within the sample chamber 28 and through the optical filter 40. If the non-dispersive infrared sensor 42 detects light within the wavelength range passed by the optical filter 40, this may indicate that the refrigerant within the sample chamber is counterfeit.

The first sensing device 16 may further include a controller 44 operably coupled to the non-dispersive infrared sensor 42, and the infrared lamp 38. The controller 44 can be configured to receive data from the non-dispersive infrared sensor 42 and provide a power signal to the infrared lamp 38.

The first sensing device 16 can further include a reference chamber 46 disposed adjacent to the sample chamber 28, wherein the reference chamber 46 includes a reference sample disposed therein. The reference chamber 46 can be configured to provide a reference for the non-dispersive infrared sensor 42 in order to improve the accuracy of a reading of the refrigerant within the sample chamber 28. For example, reference sample may include a refrigerant (e.g., R134a) or air to name a couple of non-limiting examples.

Figure 4:
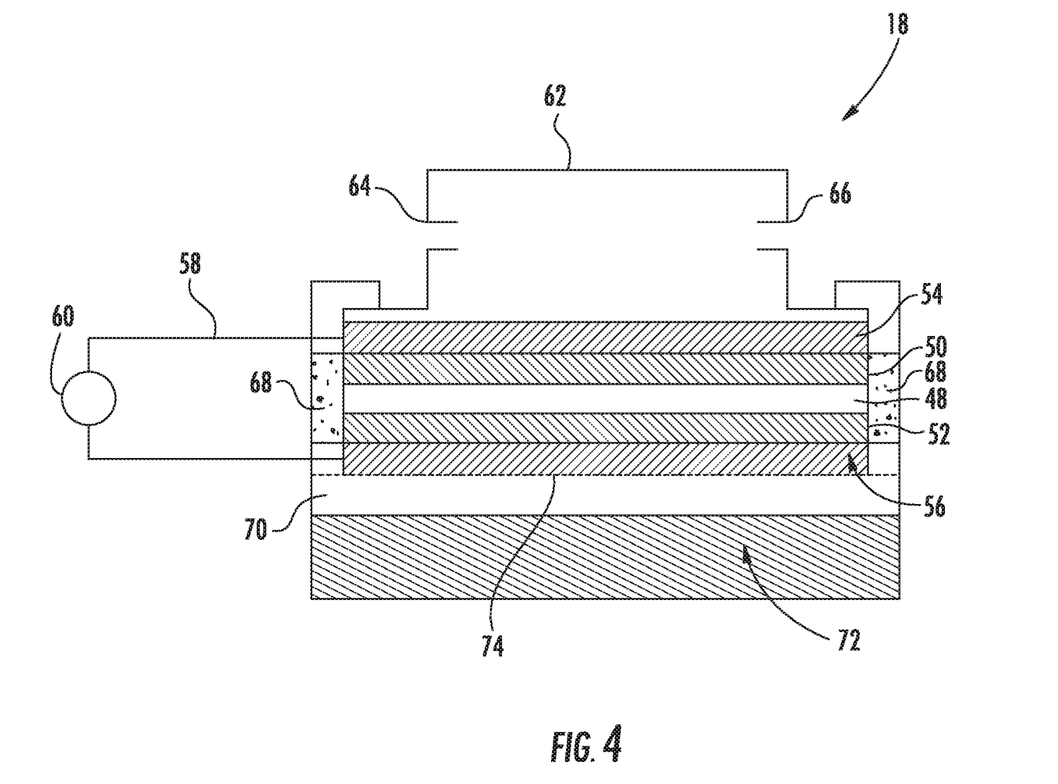
FIG. 4 illustrates a schematic diagram of a constituent electrochemical sensor.

FIG. 4 illustrates the second sensing device 18. In the embodiment shown, the second sensing device 18 includes a membrane electrode assembly (MEA) consisting of a solid polymer electrolyte (SPE) (i.e., ion conducting polymer or ion conducting polymer infiltrated porous matrix) 48 disposed between a sensing electrode 50 and counter electrode 52. Current collectors/gas diffusion media 54 and 56 are attached to the electrodes and are connected to circuit 58, which includes a measurement and/or control device 60. In some embodiments, an optional reference electrode (not shown) may be in contact with the SPE 48 and electrically connected to measurement and/or control device 60 to enable a compact and integrated multiple sensor device.

Housing 62 includes openings 64 and 66 for refrigerant to flow therethrough. The edges of the MEA are sealed against seal 68 formed of a seal material such as rubber, to name just one non-limiting example. The seal 68 ensures that the test gas and reference gas are maintained on opposing sides of the MEA, although other techniques known in the art (e.g., disposing the electrochemical sensor 18 in a frame (not shown) that is sealed to the edges of the housing) can be used.

The current collectors 54, 56 can be formed from a porous conductive mesh or felt, and are depicted with thickness so that they can also function as gas diffusion media enabling the refrigerant tested and a reference gas (e.g., air) to reach the surface of the electrodes 50, 52. The current collector/gas diffusion mediums 54 and 56 associated with the sensing electrode 50 and counter electrode 52, respectively, can be formed from an oxidation-resistant material such as graphitized carbon, titanium, noble metals (e.g. ruthenium, rhodium, palladium, silver, gold, osmium, iridium, platinum and the like), or stainless steel, to name just a few non-limiting examples. Measurement and/or control device 60 can include a voltmeter, an ampere meter, a potentiostatic circuit, a microprocessor, an electronic control unit (ECU), or a combination including at least one of the foregoing, or a similar electronic device with integrated voltage and or amperage measurement functions and which can also apply a voltage bias between the sensing electrode 50 and counter electrode 52 during operation of the electrochemical sensor 18.

The second sensing device 18 can further include a sealed chamber 70, which also contains a liquid material such as an aqueous salt or acid solution 72, which can be isolated from contact with the counter electrode 52 by a gas-permeable membrane 74. The liquid material is configured to regulate a humidity value within the sealed chamber 70. For example, the humidity value may be regulated at a value less than or equal to approximately 60 percent relative humidity.

Figure 5:
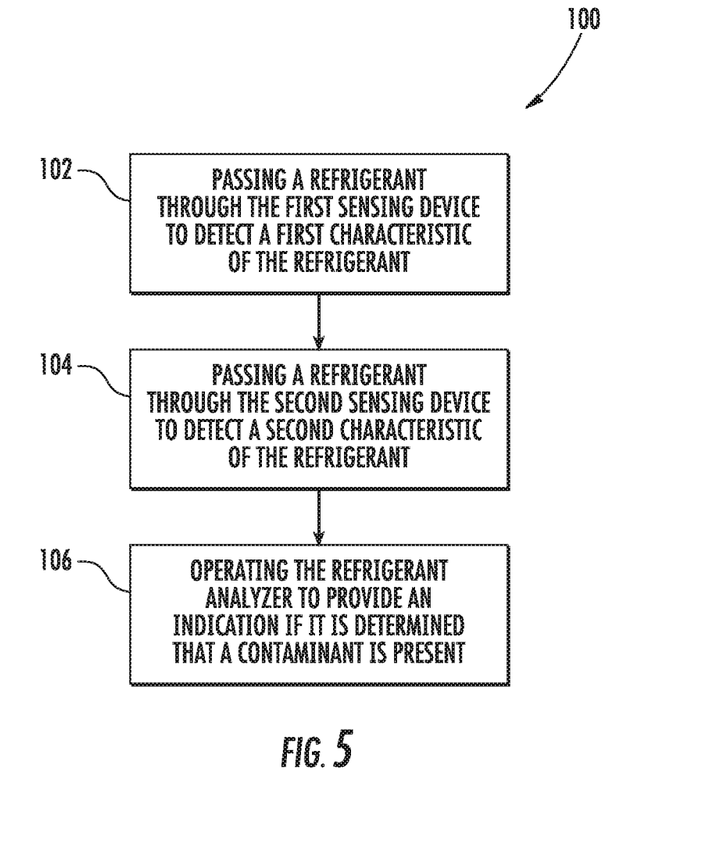
FIG. 5 illustrates a schematic flow diagram of a method of detecting a refrigerant of interest.

FIG. 5 illustrates a schematic flow diagram of a method, generally indicated at 100, for detecting a refrigerant of interest (e.g., a counterfeit refrigerant such as R40 or the like) utilizing the refrigerant analyzer 10. The method 100 includes step 102 of circulating a refrigerant through the first sensing device 16 to detect the first characteristic of the refrigerant. For example, with reference to FIGS. 1 and 3, refrigerant vessel 14 is operably coupled to the refrigerant analyzer 12, and the refrigerant flows from the refrigerant vessel 14 through the first valve 20 into the first sensing device 16. The first sensing device 16 operates the non-dispersive infrared sensor 42 to detect energy levels at a wavelength less than or equal to approximately 15,500 nanometers, for example, a wavelength greater than or equal to approximately 13,000 nanometers and less than or equal to approximately 14,400 nanometers.

As the refrigerant flows through the sample chamber 28, controller 44 operates the infrared lamp 38 to shine light through the sample chamber 28. Optical filter 40 transmits the wavelengths less than approximately 15,500 nanometers, or in some embodiments wavelength greater than or equal to approximately 13,000 nanometers and less than or equal to approximately 14,400 nanometers. The non-dispersive infrared sensor 42 detects the wavelengths that are allowed to pass through optical filter 40. It will be appreciated that wavelengths detected within the range of 13,020 nanometers-14,400 nanometers are indicative of counterfeit refrigerant R40 present in the refrigerant vessel 14.

Step 102 can further include circulating the refrigerant through a dry scrubber 24. In scenarios where a contaminant is undetectable within the second sensing device 18, the refrigerant is passed through a scrubber 24. For example, with reference to FIG. 2, the refrigerant enters the refrigerant analyzer through the first valve 20, and directed to the scrubber 24, where the scrubber 24 removes some impurities within the refrigerant before circulating through the first sensing device 16.

The method 100 further includes step 104 of circulating the refrigerant through the second sensing device 18 to detect the second characteristic of the refrigerant. For example, with reference to FIGS. 1 and 4, the refrigerant continues through the second sensing device 18, where the control device 60 measures a sensed output value, for example a voltage or current at the sensing electrode 54 relative to the counter electrode 56. The control device 60 determines a measured concentration of a contaminant within the refrigerant based on the sensed output value.

The method 100 further includes step 106 of operating the refrigerant analyzer 12 to provide an indication if it is determined that a contaminant is present and its concentration range is estimated using the apparatus and methods disclosed herein. For example, the first sensing device 16 and the second sensing device 18 may independently generate a signal indicating the presence of a contaminant. The output of the first sensing device 16 and the second sensing device 18 can be analyzed to accurately identify and quantify the impurities, as shown in FIGS. 6 and 7.

Alternatively, the first sensing device 16 and the second sensing device 18 may transmit data to the processor 22. As shown in FIGS. 6 and 7, the processor 22 may analyze the data received by the first sensing device 16 and the second sensing device 18 to determine the presence of a contaminant within the refrigerant.

Figure 6:
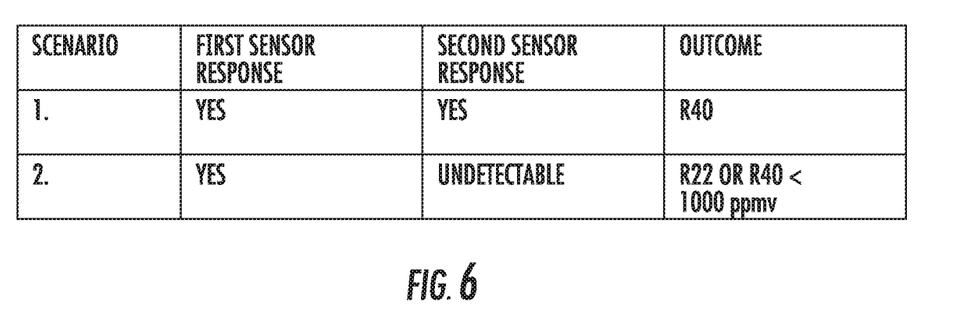
FIG. 6 illustrates a logic chart for detecting a refrigerant impurity.

FIG. 6 illustrates logic which can be used within the refrigerant analyzer 12. In Scenario 1, the first sensing device 16 and the second sensing device 18 generate a response to the refrigerant having a contaminant within the parameters defined herein. As an example, the processor 22 may generate a signal indicating the presence of R40. In Scenario 2, the first sensing device 16 generates a response to a contaminant, but the contaminant is undetectable in the second sensing device 18, the processor 22 may generate a signal indicating the presence of R40 or R22 at a concentration level less than 1000 ppmv or a detection limit associated with the second sensing device 18. If the output from Scenario 1 and 2 is deemed inadequate, an embodiment as illustrated in FIG. 2 is employed to identify contaminants. This scheme is illustrated as Scenario 3 in FIG. 7.

Figure 7:
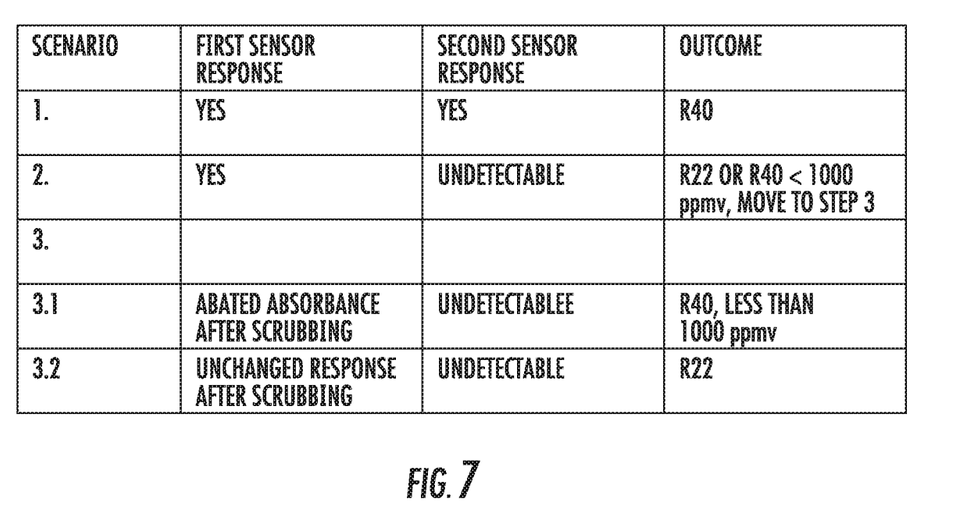
FIG. 7 illustrates a logic chart for identifying and quantifying refrigerant impurities with species scrubbing function.

FIG. 7 illustrates embodiments of the logic within the refrigerant analyzer 12, as shown in FIG. 2. In Scenario 2, if the output of first sensing device 16 doesn't provide sufficient resolution to distinguish R40 from R22 based on the absorbance characteristic to these species, additional analysis should be conducted with the assistance of the scrubber 24. The determination logic is presented as Scenario 3 in FIG. 7.

In Scenario 3.1 if there is abated absorbance of the wavelengths after the refrigerant has passed through the scrubber 24, the processor 22 may generate a signal indicating the presence of both R40 and R22 at a concentration level less than 1000 ppmv. In Scenario 3.2 if there is no change after the refrigerant has passed through the scrubber 24, the processor 22 may generate a signal indicating the presence of only R22 at a concentration level less than 1000 ppmv or a detection limit associated with the second sensing device 18. In some embodiments, the processor 22 may generate a signal indicating the presence of an impurity such as R22, R40, or a combination including at least one of the foregoing without indicating a concentration level. In this way, the refrigerant analyzer 12 can provide a binary indication of whether a refrigerant is contaminated with counterfeit refrigerant or not.

It will therefore be appreciated that the present embodiments include a refrigerant analyzer 12 combining a highly sensitive first sensing device 16 and a highly selective second sensing device 18 to generate differential responses to enable the detection of contaminants within a refrigerant. The highly sensitive first sensing device 16 can detect concentrations of an impurity (e.g. R22, R40, and the like) as low as 10 ppmv, for example concentrations from 10 ppmv to 10,000 ppmv, or 10 ppmv to 2000 ppmv, or 10 ppmv to 1,000 ppmv. The highly selective second sensing device 18 can have sensitivity (i.e. signal intensity per unit concentration) to R40 that is infinite times that of other impurities that may be present in a refrigerant sample passing through the refrigerant analyzer 12, for example 2 to 1000 times more sensitive.

Embodiment 1: a method of detecting impurities in a refrigerant utilizing a refrigerant analyzer, wherein the refrigerant analyzer includes a first sensing device in flow communication with a second sensing device, the method including passing a refrigerant through the first sensing device to detect a first characteristic of the refrigerant, and passing the refrigerant through the second sensing device to detect a second characteristic of the refrigerant.

Embodiment 2: the method of embodiment 1, wherein the first characteristic comprises a wavelength.

Embodiment 3: the method of any of the preceding embodiments, wherein the first characteristic comprises a wavelength and the wavelength is less than or equal to approximately 15,500 nanometers.

Embodiment 4: the method of any of the preceding embodiments, wherein the second characteristic comprises a measured concentration level based at least in part on a sensed output.

Embodiment 5: the method of any of the preceding embodiments, wherein the second characteristic comprises a measured concentration level based at least in part on a sensed output and the measured concentration level is greater than or equal to approximately 1000 ppmv.

Embodiment 6: the method of any of the preceding embodiments further comprising passing the refrigerant through a scrubber.

Embodiment 7: the method of any of the preceding embodiments, further comprising passing the refrigerant through the scrubber and wherein the scrubber comprises a packing material comprising alumina.

Embodiment 8: the method of any of the preceding embodiments, further comprising first passing the refrigerant through the scrubber.

Embodiment 9: the method of any of the preceding embodiments, further comprising splitting the refrigerant into a first refrigerant stream and a second refrigerant stream and passing the first refrigerant stream through the scrubber while not passing the second refrigerant stream through the scrubber.

Embodiment 10: the method of any of the preceding embodiments further comprising operating the refrigerant analyzer to provide an indication if it is determined that a contaminant is present.

Embodiment 11: a refrigerant analyzer comprising a first sensing device, wherein the first sensing device is configured at least to determine a first characteristic of a refrigerant, and a second sensing device in flow communication with the first sensing device, the second sensing device configured at least to determine a second characteristic of the refrigerant.

Embodiment 12: the refrigerant analyzer of embodiment 11, further comprising a scrubber in flow communication with the first sensing device.

Embodiment 13: the refrigerant analyzer of embodiment 12, wherein the scrubber comprises a packing material comprising alumina.

Embodiment 14: the refrigerant analyzer of any of embodiments 11-13, wherein the first sensing device comprises a non-dispersive infrared sensor.

Embodiment 15: the refrigerant analyzer of any of embodiments 11-13, wherein the second sensing device comprises an electrochemical sensor.

Embodiment 16: the refrigerant analyzer of any of embodiments 11-15, further comprising a processor in communication with the first sensing device and the second sensing device.

Embodiment 17: the refrigerant analyzer of any of embodiments 9-16, wherein the first characteristic comprises a wavelength.

Embodiment 18: the refrigerant analyzer of embodiment 17, wherein the wavelength is less than or equal to approximately 15,500 nanometers.

Embodiment 19: the refrigerant analyzer of any of embodiments 11-18, wherein the second characteristic comprises a measured concentration level based at least in part on a sensed output.

Embodiment 20: the refrigerant analyzer of embodiment 19, wherein the measured concentration level is greater than or equal to approximately 1000 ppmv.

Embodiment 21: the refrigerant analyzer of any of embodiments 11-20, wherein the scrubber is fluidly upstream of the first sensing device.

Embodiment 22: the refrigerant analyzer of any of embodiments 11-21, wherein the scrubber is fluidly upstream of the second sensing device.

Embodiment 23: the refrigerant analyzer of any of embodiments 11-22, further comprising a flow regulator operably coupled to the scrubber and the second sensing device, wherein the flow regulator is configured to create a first refrigerant stream and a second refrigerant stream.

Embodiment 24: the refrigerant analyzer of embodiment 23, wherein the first refrigerant stream passes through the scrubber and the second refrigerant stream does not pass through the scrubber.

While the present disclosure has been illustrated and described in detail in the drawings and foregoing description, the same is to be considered as illustrative and not restrictive in character, it being understood that only certain embodiments have been shown and described and that all changes and modifications that come within the spirit of the present disclosure are desired to be protected.

What is claimed is:

1. A method of detecting impurities in a refrigerant utilizing a refrigerant analyzer, wherein the refrigerant analyzer includes a first sensing device in flow communication with a second sensing device, the method comprising:
   splitting the refrigerant into a first refrigerant stream and a second refrigerant stream and passing the first refrigerant stream through a scrubber while not passing the second refrigerant stream through the scrubber;
   passing the first refrigerant stream through the first sensing device to detect a first characteristic of the refrigerant of the first refrigerant stream;
   passing the second refrigerant stream through the first sensing device to detect a first characteristic of the refrigerant of the second refrigerant stream;
   passing the second refrigerant stream through the second sensing device to detect a second characteristic of the refrigerant of the second refrigerant stream.

2. The method of claim 1, wherein the first characteristic comprises absorption of a wavelength of light by the refrigerant.

3. The method of claim 1, wherein the first characteristic comprises absorption of a wavelength of light by the refrigerant and the wavelength is less than or equal to approximately 15,500 nanometers.

4. The method of claim 1, wherein the second characteristic comprises a measured concentration level based at least in part on a sensed output of the second sensing device.

5. The method of claim 1, wherein the second characteristic comprises a measured concentration level based at least in part on a sensed output and the measured concentration level is greater than or equal to approximately 1000 ppmv.

6. The method of claim 1, wherein the scrubber comprises a packing material comprising alumina.

7. The method of claim 1 further comprising:
   operating the refrigerant analyzer to provide an indication if it is determined that a contaminant is present.

8. The method of claim 1, wherein the first sensing device comprises a non-dispersive infrared sensor and the second sensing device comprises an electrochemical sensor.

9. A refrigerant analyzer comprising:
   a scrubber;
   a first sensing device;
   a flow regulator operably coupled to the scrubber and the first sensing device, wherein the flow regulator is configured to create a first refrigerant stream and a second refrigerant stream;
   wherein the first sensing device is configured at least to determine a first characteristic of a refrigerant of the first refrigerant stream and the second refrigerant stream;
   a second sensing device in flow communication with the first sensing device, the second sensing device configured at least to determine a second characteristic of the refrigerant of the second refrigerant stream;
   wherein the first refrigerant stream passes through the scrubber and the second refrigerant stream does not pass through the scrubber.

10. The refrigerant analyzer of claim 9, wherein the scrubber comprises a packing material comprising alumina.

11. The refrigerant analyzer of claim 9, further comprising a processor in communication with the first sensing device and the second sensing device.

12. The refrigerant analyzer of claim 9, wherein the first characteristic comprises absorption of a wavelength of light by the refrigerant.

13. The refrigerant analyzer of claim 12, wherein the first characteristic comprises absorption of a wavelength of light by the refrigerant and the wavelength is less than or equal to approximately 15,500 nanometers.

14. The refrigerant analyzer of any of claim 9, wherein the second characteristic comprises a measured concentration level based at least in part on a sensed output.

15. The refrigerant analyzer of claim 14, wherein the measured concentration level is greater than or equal to approximately 1000 ppmv.

16. The refrigerant analyzer of claim 9, wherein the first sensing device comprises a non-dispersive infrared sensor and the second sensing device comprises an electrochemical sensor.

\* \* \* \* \*